US009011947B2

(12) United States Patent
Carder et al.

(10) Patent No.: US 9,011,947 B2
(45) Date of Patent: Apr. 21, 2015

(54) METHOD OF PREPARING HIGHLY DISPERSIBLE WHOLE GRAIN FLOUR WITH AN INCREASED AVENANTHRAMIDE CONTENT

(71) Applicant: The Quaker Oats Company, Chicago, IL (US)

(72) Inventors: Gary Carder, Barrington Hills, IL (US); Robert E. Chatel, Barrington, IL (US); YiFang Chu, Glenview, IL (US); Yongsoo Chung, Palatine, IL (US); Justin A. French, Frisco, TX (US); Marianne O'Shea, Chicago, IL (US); Bernadus Jan-Willem Van Klinken, Barrington, IL (US)

(73) Assignee: The Quaker Oats Company, Chicago, IL (US)

( * ) Notice: Subject to any disclaimer, the term of this patent is extended or adjusted under 35 U.S.C. 154(b) by 48 days.

(21) Appl. No.: 13/833,717

(22) Filed: Mar. 15, 2013

(65) Prior Publication Data

US 2013/0209610 A1 Aug. 15, 2013

Related U.S. Application Data

(63) Continuation-in-part of application No. 12/814,610, filed on Jun. 14, 2010.

(60) Provisional application No. 61/186,862, filed on Jun. 14, 2009.

(51) Int. Cl.
| | |
|---|---|
| *A23L 1/10* | (2006.01) |
| *A23L 1/105* | (2006.01) |
| *A23L 1/00* | (2006.01) |
| *A21D 6/00* | (2006.01) |
| *A23L 1/187* | (2006.01) |

(52) U.S. Cl.
CPC ............. *A23L 1/1041* (2013.01); *A23L 1/105* (2013.01); *A23L 1/002* (2013.01); *A21D 6/006* (2013.01); *A23L 1/1055* (2013.01); *A23L 1/187* (2013.01); *A21D 6/00* (2013.01); *A21D 6/003* (2013.01)

(58) Field of Classification Search
CPC ............................... A23L 1/1041; A23L 1/105
USPC .................................................. 426/28, 622
See application file for complete search history.

(56) References Cited

U.S. PATENT DOCUMENTS

| | | | |
|---|---|---|---|
| 3,317,402 A | 5/1967 | Smith | |
| 3,851,085 A | 11/1974 | Rodgers | |
| 3,869,558 A | 3/1975 | Hampton | |
| 3,925,343 A | 12/1975 | Hampton | |
| 3,958,016 A | 5/1976 | Galle | |
| 4,038,427 A | 7/1977 | Martin | |
| 4,171,384 A | 10/1979 | Chwalek | |
| 4,266,027 A | 5/1981 | Muller | |
| 4,282,319 A | 8/1981 | Conrad | |
| 4,330,625 A | 5/1982 | Miller | |
| 4,377,602 A | 3/1983 | Conrad | |
| 4,431,674 A | 2/1984 | Fulger | |
| 4,435,429 A | 3/1984 | Burrows | |
| 4,435,430 A | 3/1984 | Fulger | |
| 4,656,040 A | 4/1987 | Fulger | |
| 4,710,386 A | 12/1987 | Fulger | |
| 4,777,056 A | 10/1988 | Buhler | |
| 4,834,988 A | 5/1989 | Karwowski | |
| 4,834,989 A | 5/1989 | Bolles | |
| 4,996,063 A | 2/1991 | Inglett | |
| 4,999,208 A | 3/1991 | Lengerich | |
| 5,021,248 A | 6/1991 | Stark | |
| 5,082,673 A | 1/1992 | Inglett | |
| 5,225,219 A | 7/1993 | Inglett | |
| 5,656,317 A | 8/1997 | Smits | |
| 5,846,786 A | 12/1998 | Senkeleski | |
| 5,888,548 A | 3/1999 | Wongsuragrai | |
| 6,013,289 A | 1/2000 | Blank | |
| 6,054,302 A | 4/2000 | Shi | |
| 6,244,528 B1 | 6/2001 | Wallis | |
| 6,287,621 B1 | 9/2001 | Lacourse | |
| 6,551,366 B1 | 4/2003 | D'Souza | |
| 6,720,022 B1 | 4/2004 | Arnaut | |
| 6,723,358 B1 | 4/2004 | van Lengerich | |
| 6,759,077 B1 | 7/2004 | Lewis | |
| 7,419,694 B2 | 9/2008 | Korolchuk | |
| 7,425,344 B2 | 9/2008 | Korolchuk | |
| 2002/0187224 A1 | 12/2002 | Haefliger | |
| 2003/0170362 A1 | 9/2003 | Manning | |
| 2004/0028797 A1 | 2/2004 | Squire | |

(Continued)

FOREIGN PATENT DOCUMENTS

| | | |
|---|---|---|
| EP | 0609169 | 8/1994 |
| EP | 0897673 | 2/1999 |

(Continued)

OTHER PUBLICATIONS

Vasanthan, T., et al., Dextrinization of Starch in Barley Flours with Thermostable alpha-Amylase by Extrusion Cooking, © WILEY-VCH Verlag GmbH, 69451 Weinheim, Dec. 1, 2001, pp. 616-622.

(Continued)

*Primary Examiner* — Hamid R Badr
(74) *Attorney, Agent, or Firm* — Banner & Witcoff, Ltd.

(57) ABSTRACT

A method of preparing a highly dispersible whole grain oat flour by hydrolyzing, milling and agglomerating grain flour to arrive at a whole grain oat flour having an increased avenanthramide content compared to native oat flour.

13 Claims, 6 Drawing Sheets

(56) References Cited

U.S. PATENT DOCUMENTS

| | | |
|---|---|---|
| 2004/0140584 A1 | 7/2004 | Wang |
| 2004/0151805 A1 | 8/2004 | Gao |
| 2004/0156971 A1* | 8/2004 | Wuersch et al. ............ 426/591 |
| 2004/0258829 A1 | 12/2004 | Zheng |
| 2005/0064080 A1 | 3/2005 | Creighton |
| 2005/0181114 A1 | 8/2005 | Bruemmer |
| 2006/0013940 A1 | 1/2006 | Mueller |
| 2006/0251791 A1 | 11/2006 | Rubio |
| 2006/0280838 A1 | 12/2006 | Kvist |
| 2006/0286269 A1 | 12/2006 | Shah |
| 2007/0014892 A1 | 1/2007 | Mitchell |
| 2007/0059340 A1 | 3/2007 | Bello |
| 2007/0104854 A1* | 5/2007 | Foster et al. ................. 426/620 |
| 2007/0178199 A1 | 8/2007 | Minor |
| 2007/0184175 A1 | 8/2007 | Rubio |
| 2007/0212472 A1 | 9/2007 | Holenstein |
| 2007/0243301 A1 | 10/2007 | Barnett |
| 2007/0292583 A1 | 12/2007 | Haynes |
| 2008/0003340 A1 | 1/2008 | Karwowski |
| 2008/0008801 A1 | 1/2008 | Barnekow |
| 2008/0131582 A1 | 6/2008 | Karwowski |
| 2008/0171114 A1 | 7/2008 | Rodriguez |
| 2008/0260909 A1 | 10/2008 | Chung |
| 2009/0053771 A1 | 2/2009 | Dale |
| 2009/0148562 A1 | 6/2009 | Lin |
| 2009/0181128 A1 | 7/2009 | Blumenthal |
| 2009/0238935 A1 | 9/2009 | Haynes |
| 2009/0311376 A1 | 12/2009 | Rao |

FOREIGN PATENT DOCUMENTS

| | | |
|---|---|---|
| EP | 0634106 | 4/1999 |
| EP | 0806434 | 5/2003 |
| EP | 1782699 | 5/2007 |
| GB | 1168692 | 10/1969 |
| WO | 9210106 | 6/1992 |
| WO | 03011052 | 2/2003 |
| WO | 2004086878 | 10/2004 |
| WO | 2009127687 | 10/2009 |
| WO | 2010053653 A1 | 5/2010 |
| WO | 2010108277 A1 | 9/2010 |
| WO | 2010147892 A1 | 12/2010 |

OTHER PUBLICATIONS

Gutkoski, L.C., et al., "Effect of Extrusion Process Variables on Physical and Chemical Properties of Extruded Oat Products", Plant Foods for Human Nutrition, © 2000 Kluwer Academic Publishers, pp. 315-325, Dec. 1, 1999.

Written Opinion and International Search Report for PCT Application No. PCT/US2010/038506 mailed Aug. 10, 2010, 18 pages.

Australian Patent Application No. 2010260219 Office Action dated Aug. 23, 2012.

Chinese Patent Application No. 201080022395.5 Office Action dated Nov. 8, 2012.

Canadian Patent Application No. 2,761,566 Office Action dated Dec. 27, 2012.

Russian Patent Application No. 2011145771 Office Action mailed Jan. 21, 2013.

Chinese Patent Application 200880025660.8, Office Action dated Aug. 2, 2012.

Zhang Haodong, "Starch Article Technology", Jilin Science and Technology Press, dated Feb. 29, 2008.

Gualberto, D.G. et al., Effect of extrusion processing on the soluble and insoluble fiber, and phytic acid contents of cereal brans, dated Sep. 28, 1997.

Wang, Ming-chun, et al, Extrusion Technology Applied in the Nutritional Health Foods, College of Food Engineering & Biologic Technology, Tianjin University of Science and Technology, Tianjin 300457, pp. 63-66, dated Aug. 1, 2007, with English Abstract.

Wang Changqing, et al, Study on the Extruding Production Method of Soluble Oats Fiber, vol. 28, No. 2, pp. 45-48, dated Mar. 20, 2002, with English Abstract.

Inglett, G.E. et al. 1994. Oat beta-glucan-amylodextrin: Preliminary preparations and biological properties. plant Fd. for Human Nutrition. 45: 53-61.

Office Action for corresponding European Patent Application 09740225.9 dated May 16, 2011.

Linko YY et al: The effect of HTST—extrusion on retention of cereal alpha-amylase activity and on enzymatic hydrolisis of barley starch, Food Processing Systems, Applied Science Publ, UK, Jan. 1, 1980, pages Abstr, 4.2.25, 210-223, XP009127925, ISBN: 978-0-85334-896-2.

Anonymous: "Ovsena nahradka mlieka", XP002561727, URL:http://web.archive.org/web/20080420075151/http://www.aspsk.sk/ovsene_mlieko.htm>, retrieved from the Internet on Dec. 18, 2009, pp. 1-1, dated Apr. 20, 2008.

Anonymous: "Goldkill Instant Barley Drink", XP002561728, URL:http://web.archive.org/web/20060303003347/goldkill.com/goldkili_instant.php>, retrieved from the Internet on Dec. 28, 2009, pp. 1-2, dated Mar. 3, 2006.

Peter Koelln KGAA: "Kochjule, Hafer-Getrank mit Fruchtsaft", XP002499645, Internet Citation, URL:http://www.koelln.de/downloads/37/Kochjule.pdf>, retrieved from the Internet on Oct. 14, 2008, pp. 1-19, dated Oct. 14, 2008.

Peter Kolln KGAA: "Kolln Schmelzflocken Dinkel-Hafer", XP002499438, Internet Citation, URL:http://www.koelln.de/produkte/2/103/index.html>, retrieved from the Internet on Oct. 13, 2008, p. 1, dated Oct. 13, 2008.

Peter Kolln KGAA: "KollnFlocken Instant", XP002499437, Internet Citation, URL:http://www.koelln.de/produkte/1/15/index.html>, retrieved from the Internet on Oct. 13, 2008, p. 1, dated Oct. 13, 2008.

Office Action received for corresponding European Patent Application 09 740 225.9 mailed Oct. 11, 2010.

Russian Patent Application No. 2011145771 Office Action mailed Apr. 18, 2013.

Mexican Application No. MX/a/2011/011981 Office Action mailed Jul. 23, 2013.

Chinese Application No. 201080022395.5 Office Action mailed Oct. 14, 2013.

Mexican Application No. MX/a/2011/011981 Office Action mailed Mar. 10, 2014.

International Search Report and Written Opinion of PCT/US2014/21913 mailed Jun. 23, 2014.

MX Application No. MX/a/2011/011981 Office Action mailed Mar. 10, 2014.

EP Application No. 10727309.6 Office Action mailed Sep. 26, 2014.

MY Application No. PI2011005427 Office Action mailed Sep. 30, 2014.

\* cited by examiner

METHOD OF PREPARING HIGHLY DISPERSIBLE WHOLE GRAIN FLOUR WITH AN INCREASED AVENANTHRAMIDE CONTENT

CROSS-REFERENCE TO RELATED APPLICATIONS

This application is a continuation-in-part of U.S. patent application Ser. No. 12/814,610 filed on Jun. 14, 2010 which claims priority to U.S. Provisional Patent Application No. 61/186,862 filed on Jun. 14, 2009, the disclosure of which is expressly incorporated herein by reference.

FIELD OF THE INVENTION

The present invention relates generally to a method for preparing a highly dispersible, otherwise referred to as "soluble" whole grain flour. More specifically, the present invention relates to methods of making highly dispersible oat flour with an increased avenanthramide content.

BACKGROUND

Due to high cholesterol, obesity, and heart disease concerns, many consumers are interested in making healthier choices with respect to their diets. For this reason, a need exists to provide consumers with whole grain, low cholesterol products. However, with fast-paced lifestyles, it is difficult for consumers to prepare healthy meals or snacks. Therefore, a need also exists to provide the consumer with ready-to-eat nutritious products. Furthermore, there exists a need in the marketplace for a comestible that contains high levels of whole grains in drinkable forms.

It is desired to prepare a whole grain product that maintains its structure during processing (i.e., the starchy endosperm, germ and bran) to meet the FDA threshold necessary to justify a health claim. More specifically, it is desired to prepare a hydrolyzed whole grain flour that is highly dispersible in liquid or semi-solid media that maintains the structure of the whole grain during processing.

Attempts have been made in the food industry to provide a hydrolyzed whole grain that maintains its whole grain structure throughout processing; however, the hydrolyzed whole grain flours tend to clump, have an unacceptable mouthfeel and/or are unappealing to consumers. The present invention overcomes the aforementioned problems and provides consumers with a hydrolyzed whole grain flour that maintains its whole grain structure and nutritional value, and is highly dispersible in liquid and semi-solid media, thereby having an improved mouthfeel and improved consumer acceptance.

Avenanthramides are antioxidants uniquely found in oats. Since their first isolation in the 1980's, more than 30 congeners have been characterized and the most abundant avenanthramides in oats are 2p, 2f and 2c. These polyphenols demonstrate potent antioxidant, anti-inflammatory and anti-atherosclerotic properties, and may be beneficial to people with chronic inflammatory diseases, allergy and cardiovascular disease. Beyond the food industry, avenanthramides' benefits have also been well documented. Tranilast, an analogue of avenanthramides, has been approved for treating inflammation-related disease and the skin care product Aveeno™ is based on the proven benefits of avenanthramides.

In order to achieve beneficial effects on human health, avenanthramides must be ingested in a sufficient amount. In a 1999 Tufts University study, avenanthramides were confirmed to be bioavailable and remain bioactive in humans after ingestion. After 60 or 120 mg consumption, the maximum concentrations of total plasma avenanthramide were 168 and 560 nM, respectively. A more recent study performed by the University of Minnesota showed that consumption of avenanthramides at doses as low as 0.4 or 9.2 mg/day for 8 weeks increased plasma total antioxidant activity and had dose-response effects on several antioxidant and anti-inflammatory parameters. These effects are probably due to the accumulation and high concentration of avenanthramides in different tissues and organs.

Avenanthramide content in oat grains varies based on cultivars and food processing methods. For example, heat treatment generally reduces avenanthramide 2f, 2c, and more profoundly 2p. The processing methods that increase avenanthramide content are of great importance to help people reach health benefits through regular consumption of oat products.

Nuclear factor-kappa B (NF-κB) is a family of eukaryotic nuclear transcription factors that regulate the transcription of DNA and are involved in the activation of genes related to inflammatory and immune responses. The regulation of the inflammatory response by NF-κB occurs via the enhancement of the expression of genes encoding proinflammatory cytokines, such as tumor necrosis factor (TNF)-α, interleukin (IL)-6, and interleukin (IL)-1β. Activation of NF-κB leads to inflammation that in turn is involved in the pathogenesis of many diseases, such as asthma, rheumatoid arthritis, and inflammatory bowel disease and is at least partially responsible for diseases such as atherosclerosis and Alzheimer's disease. Suppression of NF-κB, a regulator of the immune response to infection, is key in limiting the proliferation of cancer cells and reducing the level of inflammation. Studies have shown that avenanthramides inhibit NF-κB activation.

BRIEF SUMMARY

Aspects of the invention relate to soluble oat flour having an increased avenanthramide content. Additional aspects of the present invention relate to a method for preparing a hydrolyzed whole grain flour. In one aspect of the present invention, an enzyme hydrolyzes the whole grain flour while maintaining the integrity of the whole grain.

In another aspect of the instant invention, a whole grain is finely milled and subsequently agglomerated to improve dispersibility of the grain in liquid or semi-solid media. The grain used for agglomeration may be untreated/native, pre-gelatinized, or hydrolyzed.

These and other aspects, along with advantages and features of the present invention herein disclosed, will become apparent through reference to the following description. Furthermore, it is to be understood that the features of the various embodiments described herein are not mutually exclusive and can exist in various combinations and permutations.

BRIEF DESCRIPTION OF THE DRAWINGS

Numerous other objects, features and advantages of the present invention will be apparent based upon the following description of the drawings.

DETAILED DESCRIPTION OF THE INVENTION

The present invention relates to soluble oat flour having an increased level of avenanthramides over soluble oat flour prepared in accordance with prior known methods. In particular, the present invention relates to a method for preparing a highly dispersible whole grain flour. Moreover, the present invention relates to a hydrolyzed whole grain flour that maintains its whole grain status throughout processing and is highly dispersible in liquid and semi-solid media. The whole grain may be any suitable cereal grain such as oat, wheat, corn (maize), rice, barley, rye, quinoa, sorghum, millet, triticale or combinations thereof. As set forth herein, "whole grain status," "whole grain standard of identity," "standard of identity as whole grain" or "maintaining the integrity of the whole grain" shall mean whole grains consisting of the intact, ground, cracked or flaked caryopsis, whose principal anatomical components—the starchy endosperm, germ and bran—are present in the same relative proportions as they exist in the intact caryopsis.

The dispersibility of the flour was measured in water observing formation of a lump and size of the lumps and formation of the lumps on the top and bottom of the water after stirring for five (5) seconds. With respect to the flour made in accordance with the instant disclosure, no lumps were present or formed after stirring the mixture for about five (5) seconds.

Figure 1:
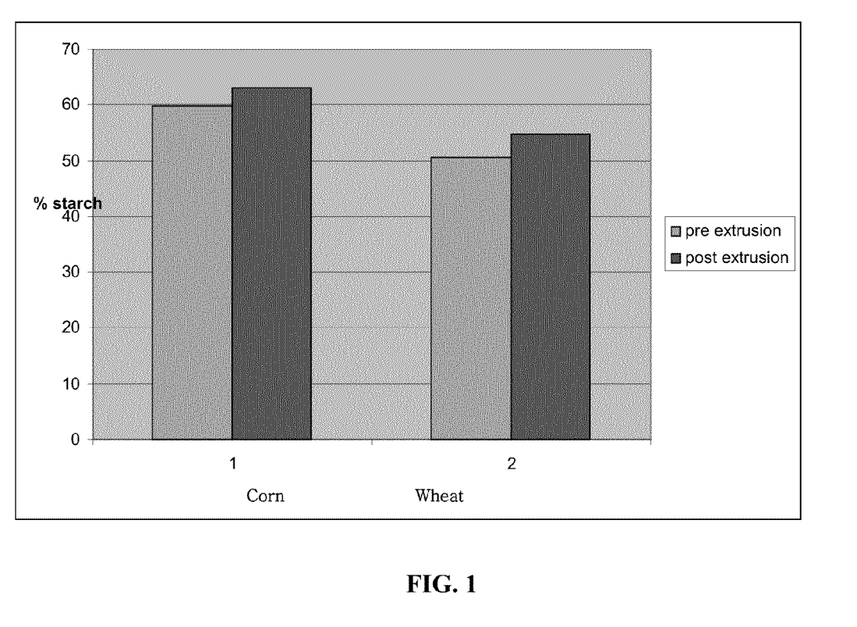
FIG. 1 illustrates the comparison of the pre-extrusion and the post-extrusion starch values of corn and whole wheat flour prepared in accordance with the present invention.
Figure 2:
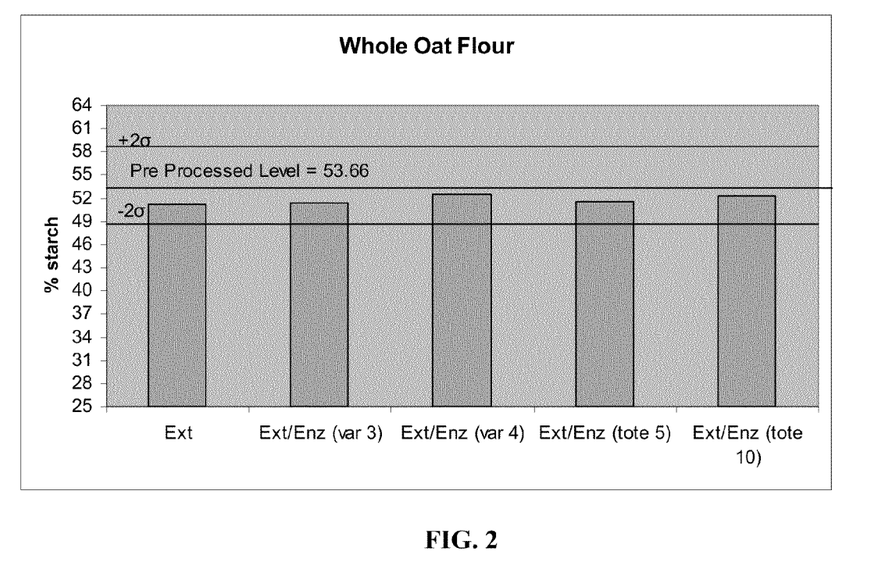
FIG. 2 illustrates a comparison of the starch content of whole oat flour samples pre and post processing via extrusion and pre and post processing via extrusion and enzyme addition.

In one aspect of the present invention, the method of hydrolyzing the whole grain flour includes hydrolyzing, milling, and agglomerating the whole grain flour. More specifically, the flour is hydrolyzed using an enzyme. The enzyme used in accordance with the present invention allows the whole grain flour to maintain its standard of identity as whole grain. One example of an enzyme that hydrolyzes the whole grain flour while maintaining the integrity of the whole grain is alpha amylase. The enzyme used in accordance with the present invention may be any enzyme that hydrolyzes the alpha 1-4 bonds on the amlyopectin molecule that makes up the starch portion of the whole grains. The enzyme may also hydrolyze the amylose molecules of the whole grain. Suitable enzymes include α-amylase in the range of about 0.01-0.5%, for example about 0.1-0.2%. In one aspect of the present disclosure, the α-amylase used may be Validase BAA 1000L having approximately 1,000,000 MWU/g (MWU—Modified Wohlgemuth Unit). One of ordinary skill in the art of the food sciences would recognize that one or more enzymes may be used in accordance with the present invention. Testing and analysis of whole grain flours, such as wheat flour and oat flour using the method set forth herein, has verified and validated that the starch molecules are maintained throughout processing. The results of this testing are illustrated in FIGS. 1 and 2. As shown in Table 1 below, any change of the food constituents made in accordance with this aspect of the invention is negligible at best.

TABLE 1

|  | Whole oat flour | Hydrolyzed oat flour |
| --- | --- | --- |
| β-glucan, % | 4.19 | 4.12 |
| TDF, % | 10.5 | 11.99 |
| Fat, % | 7.49 | 6.77 |
| Protein, % | 14.07 | 13.81 |
| Starch, % | 65.02 | 66.16 |
| Maltose, % | 0 | 0.26 |

By maintaining the whole grain status throughout processing, "whole grain" health claims may be made with respect to the hydrolyzed whole grain flour made in accordance with the present invention. Furthermore, the nutritional backbone of the whole grain is maintained throughout processing; therefore, the hydrolyzed whole grain flour produced by the method set forth herein provides the same nutritional benefits as un-hydrolyzed whole grain flours.

In one aspect of the present invention, the dry whole grain flour is preconditioned by hydrating a whole grain flour starting mixture with water and steam to an overall moisture of about 30% (dw). At least one enzyme that hydrolyzes the whole grain flour while maintaining the integrity of the whole grain is then added to the mixture. In another aspect of the present invention, the dry whole grain flour may be mixed with sugar, maltodextrin and/or mixed tocopherols.

After a suitable amount of time to hydrate the whole grain flour, the enzyme-treated mixture is then subjected to an extrusion process to continue to break down and hydrolyze the whole grain flour and to gelatinize and cook the mixture to form a cooked hydrolyzed whole grain dough. The mixture resides in the extruder for a time sufficient to gelatinize and cook the starch, but not long enough to dextrinize to the point where it is no longer whole grain or otherwise modify the starch to void the whole grain aspect, generally at least 1 minute, typically, about 1 to about 1.5 minutes. Generally, the material is heated from an initial inlet temperature to a final exit temperature in order to provide the energy for starch gelatinization. In one aspect of the present invention, the dough pressure at the exit of the cooking extruder is about 900-1000 psi. Prior to exiting the cooking extruder, the dough is heated to about 260-300° F., for instance about 265-285° F. to fully deactivate the enzyme.

Starch gelatinization requires water and heat. The gelatinization temperature range for oats is 127° F. to 138° F. (53-59° C.). If the moisture is less than about 60% then higher temperatures are required.

Heat may be applied through the extruder barrel wall such as with a jacket around the barrel through which a hot medium like steam, water or oil is circulated, or electric heaters imbedded in the barrel. Typically the extrusion occurs at barrel temperatures between 140° F. and 350° F., for example between 175° F. and 340° F., more specifically about 180° F.-300° F.

Heat is also generated within the material by friction as it moves within the extruder by the dissipation of mechanical energy in the extruder, which is equal to the product of the viscosity and the shear rate squared for a Newtonian fluid. Shear is controlled by the design of the extruder screw(s) and the screw speed. Viscosity is a function of starch structure, temperature, moisture content, fat content and shear. The temperature of the dough increases in the extruder to approximately 212° F. and 300° F.

Low shear is applied to the mixture in the extruder. As the enzyme has preconditioned the starch to about 30% moisture, high shear is not required for this process. It can also increase the dough temperature excessively, which can overcook it resulting in too much cooked grain flavor. It is noted that the barrel temperature and the dough temperature may be different.

The process balances limiting the dough temperature to avoid too much cooked grain flavor and to keep the enzyme active. The process is balanced such that the dough temperature rises to a sufficient temperature to deactivate the enzyme. Such temperatures are at least 280° F., generally 212° F. to 300° F. As a skilled artisan would appreciate, the temperature used to deactivate the enzyme is dependent on the time it is held at this temperature. A low shear extrusion process is characterized relative to high shear extrusion by high moisture and a low shear screw design versus low moisture and a high shear screw design.

Any suitable extruder may be used including suitable single screw or twin screw extruders. Typical, but not limiting, screw speeds are 200-300 rpm. As one of ordinary skill in the art would recognize, screw speed is dependent upon the screw design.

The resulting product may be pelletized using a forming extruder and dried. In one aspect of the present invention the process takes about 9-10 minutes from the preconditioner step through the extruder and forming extruder. Moreover, the pellets may be finely milled to about 50-200 microns. One type of milling process that can be used to finely mill the pellets includes gradual reduction roller mill processing. The pellets may be dried to about 8±2% moisture prior to milling. Finally, the finely milled hydrolyzed grain flour may be agglomerated to about 150-700 microns. Fine milling of the pellets improves the mouthfeel of the resulting hydrolyzed oat flour and therefore improves consumer acceptance of the resulting product.

The agglomeration step post-milling is advantageous in that it optimizes and drastically improves dispersibility and lends itself to many applications for preparing comestible products. In one aspect of the present invention, the fine whole grain particles are agglomerated using a 2% sugar binder solution. For example, the agglomerated hydrolyzed grain flour can be added to, and is highly dispersible in, liquid and semi-solid media such as water, milk, juice, yogurts, puddings and other drinkable snack forms. Moreover, the agglomerated hydrolyzed grain flour made in accordance with the present invention makes it easy for consumers to effortlessly and efficiently stir the flour into the liquid or semi-solid of their choosing using common household utensils due to the rapid dispersion of the hydrolyzed grain flours into these liquids or semi-solids. Moreover, the agglomerated hydrolyzed grain flour made in accordance with this invention may be dispersed into liquid media by simply shaking to mix the constituents.

In one example of the present invention, the agglomerated hydrolyzed oat flour made in accordance with the present invention exhibits the properties identified in Table 2 below:

TABLE 2

| Sieve # | Size, micron | % retained |
| --- | --- | --- |
| #20 Mesh | 841 | 0% |
| #40 Mesh | 420 | 20.4% |
| #60 Mesh | 250 | 48.7% |
| #80 Mesh | 178 | 21.2% |
| #100 Mesh | 150 | 5.8% |
| Passes thru #100 Mesh | <150 | 3.0% |
| Yield | | 99.5% |
| Density | 0.4 | gram/cc |
| Moisture | 8.52 | % |

In another aspect of the present invention, untreated/native whole grain is finely milled to a particle size of about 50-420 microns, such as about 50-200 microns. These finely milled particles are then agglomerated to about 150-1000 microns, such as about 400-700 microns. The finely milled native whole grain flour may be agglomerated using any methods known in the industry, including, without limitation, using a sugar binder solution.

In yet another aspect of the present invention, pre-gelatinized whole grain flour is finely milled to a particle size of about 50-420 microns, such as 50-200 microns. The whole grains may be pre-gelatinized or pre-treated using any commercially acceptable means, including, without limitation steam treating and boiling. These finely milled pre-gelatinized whole grain particles are then agglomerated to about 150-1000 microns, such as 400-700 microns.

Another aspect of this invention includes finely milling one or more whole grain flours selected from the group consisting of native, pre-gelatinized and hydrolyzed whole grain flours made in accordance with this disclosure. The whole grain flours are finely milled to a particle size of about 50-420 microns, such as 50-200 microns. These finely milled pre-gelatinized whole grain particles are then agglomerated to about 150-1000 microns, such as 150-700 microns, including 400-700 microns.

Currently no methods exist to improve mouthfeel of a whole grain by reducing its particle size and subsequently agglomerating to improve dispersibility of the grain in liquid or semi-solid media. Moreover, the ability to easily shake or stir the agglomerated whole grains made in accordance with the instant invention for consumption of large amounts of whole grains is not only advantageous from a marketability and consumer acceptance standpoint, but is not known in the industry.

The agglomerated whole grain flours made in accordance with aspects of this invention maintain the whole grain status throughout processing. Therefore, "whole grain" health claims may be made with respect to the flour made in accordance with the present invention.

The highly dispersible whole grain flour prepared in accordance with the present invention may be used to provide the consumer with a drinkable grain product. For example, hydrolyzed oat flour prepared in accordance with the present invention may be added to water, milk, juice, yogurts, puddings, etc., to make a whole grain oat drinkable snack that is nutritious and easy to consume. Moreover, since the hydrolyzed whole grain flour is highly dispersible in liquids and semi-solids, the drinkable snack is also fast and easy to prepare. Similarly, the native and pre-gelatinized agglomerated flours may be added to the water, milk, juice, yogurts, puddings, etc. to make a whole grain drinkable snack.

The highly dispersible oat flour made in accordance with the processes described herein contains an increased avenanthramide level compared to unprocessed oats or native oat flour. In particular, native oat flour contains about 0.0002-0.03% total avenanthramides. Avenanthramides are polyphenols found only in oats. Avenanthramides have been shown to have significant antioxidant activity and have been linked to many beneficial health activities due to their potent antioxidant activities. In vivo testing has shown that the antioxidant capacity for avenanthramides provides health benefits such as a reduced rate of LDL oxidation thus protecting against cancers and heart disease. The structure of avenanthramide 2c is shown below:

Applicants have found that the levels of the three main avenanthramides present in oat—2c, 2p and 2f—are all increased as a result of the processes described herein. In particular, the total avenanthramide level (including 2c, 2p and 2f) is elevated by about 20-35% compared to native whole oat flour by the methods used to prepare the soluble oat flour described above.

Example 1

Figure 3A:
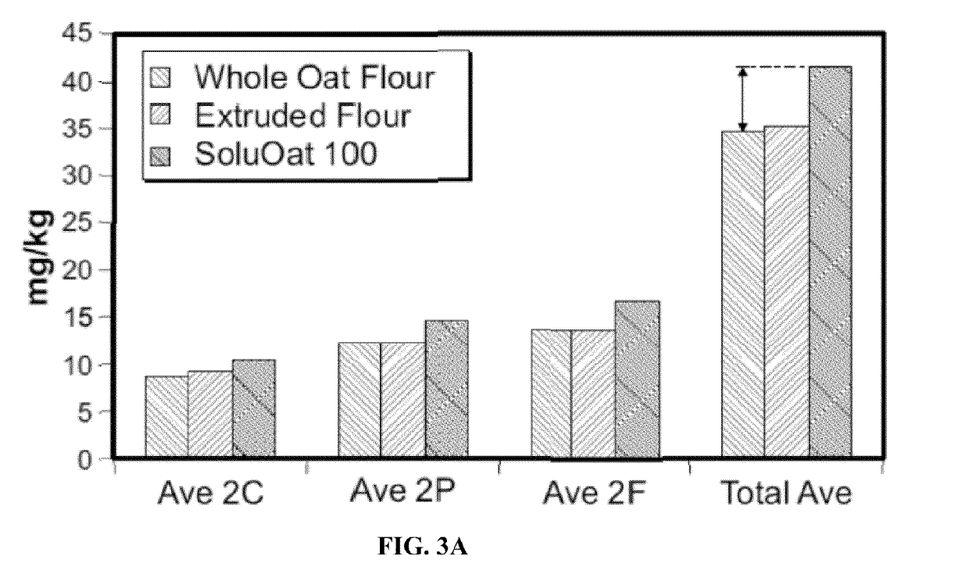
FIG. 3A compares the avenanthramide levels (2C, 2P, 2F and the total level of these avenanthramides) found in whole oat flour formed using the methods described herein ("SoluOats").
Figure 3B:
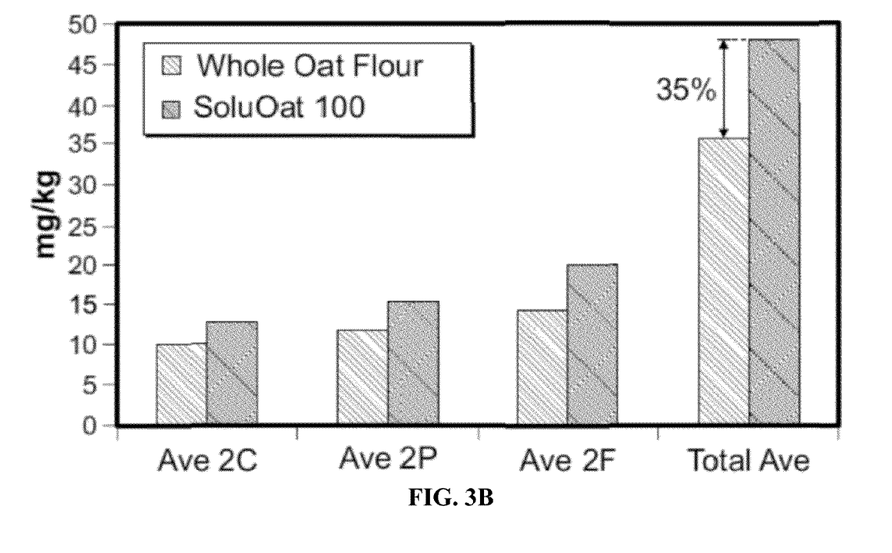
FIG. 3B compares the avenanthramide levels (2C, 2P, 2F and the total level of these avenanthramides) found in whole oat flour formed using the methods described herein ("SoluOats").

The avenanthramide levels of the resulting soluble oat flour were measured using reverse-phase HPLC. Briefly dehulled grain was extracted, dried, and re-suspended into aliquots. Aliquots were analyzed by HPLC with a C-18 column using a diode array spectrophotometer detector with detection at 340 nm. The peaks were quantified by comparison to standard curves of authentic avenanthramides. The results of this testing are illustrated in FIG. 1A and FIG. 1B. The avenanthramide content of the soluble oat flour made in accordance with the methods described herein were also found to have higher avenanthramide content than oat flour processed using solely extrusion (no enzyme.)

In particular, FIG. 3A depicts the levels of avenanthramide 2c, avenanthramide 2p, avenanthramide 2f and the total avenanthramide (2c+2p+2f) in samples of native whole oat flour, extruded flour and the SoluOat 100 flour made in accordance with the instant inventions. As used herein, "SoluOat 100," or "SoluOat 100 flour" whether singular or plural, shall mean 99.5% whole oat flour and 0.5% mixed tocopherol made in accordance with the methods set forth in the present disclosure.

As shown in FIG. 3A, the highest level of avenanthramides 2c, 2p and 2f, and the total avenanthramide content was found in the SoluOat 100 flour. In particular, the native whole oat flour was found to contain about 35 ppm total avenanthramides whereas the SoluOat flour was found to contain over 40 ppm total avenanthramides resulting in a 20% increase in the level of avenanthramides in the SoluOat 100 flour compared to the native whole oat flour. In FIG. 3B a similar test was performed testing the avenanthramide content of native whole oat flour and the SoluOat 100 flour made in accordance with the instant invention. As shown in FIG. 3B, the native whole oat flour was found to have about 35 ppm of total avenanthramides whereas the SoluOat 100 flour contained about 45 ppm total avenanthramides. Thus, the SoluOat 100 flour exhibited a 35% increase in the level of total avenanthramides compared to the native whole oat flour.

The increased avenanthramide content of the soluble oat fiber made via the embodiments described herein is surprising, since this antioxidant is a non-starch plant nutrient. However, the enzymatic process described above is used to improve dispersibility and solubility of the flour.

Subsequent analysis was also performed to distinguish the amounts of the specific avenanthramides tested under various processing conditions and the levels of avenanthramides found following processing. The table below identifies the various process conditions tested:

| | Extrusion | Enzyme Level | Moisture Level |
|---|---|---|---|
| 1 | No | 0% | Not controlled |
| 2 | Yes | 0% | 30% |
| 3 | Yes | Deactivated | 30% |
| 4 | Yes | 0.1% | 28% |
| 5 | Yes | 0.1% | 30% |
| 6 | Yes | 0.1% | 32% |
| 7 | Yes | 0.12% | 32% |
| 8 | Yes | 0.20% | 32% |

The table below identifies the avenanthramide level found in the oat flour under the different processing conditions along with the increase in avenanthramide content. All samples in the table that were extruded and hydrolyzed in accordance with the present disclosure are SoluOat 100, as defined above.

| | Ave 2c | Ave 5p | Ave 2p | Ave 2f | Total Ave |
|---|---|---|---|---|---|
| | | | (mg/kg) | | |
| WOF | 5.01 | 1.24 | 4.93 | 10.32 | 21.50 |
| WOF + EXT | 5.13 | 0.87 | 6.3 | 10.00 | 22.30 |
| WOF + EXT + DE | 5.00 | 0.89 | 5.89 | 9.60 | 21.38 |
| WOF + EXT + 0.1% E + 28% M | 5.1 | 0.85 | 6.61 | 10.33 | 22.89 |
| WOF + EXT + 0.1% E + 30% M | 5.45 | 0.85 | 7.23 | 11.25 | 24.78 |
| WOF + EXT + 0.1% E + 32% M | 5.76 | 0.95 | 7.41 | 12.21 | 26.33 |
| WOF + EXT + 0.12% E + 32% M | 5.21 | 0.73 | 6.32 | 10.62 | 22.88 |
| WOF + EXT + 0.2% E + 32% M | 5.04 | 0.77 | 6.45 | 10.33 | 22.59 |
| Increase in Ave (%) | | | | | |
| WOF | 0 | 0 | 0 | 0 | 0 |
| WOF + EXT | 2.40 | −29.84 | 27.79 | −3.10 | 3.72 |
| WOF + EXT + DE | −0.20 | −28.23 | 19.47 | −6.98 | −0.56 |
| WOF + EXT + 0.1% E + 28% M | 1.80 | −31.45 | 34.08 | 0.10 | 6.47 |
| WOF + EXT + 0.1% E + 30% M | 8.78 | −31.45 | 46.65 | 9.01 | 15.26 |
| WOF + EXT + 0.1% E + 32% M | 14.97 | −23.39 | 50.30 | 18.31 | 22.47 |
| WOF + EXT + 0.12% E + 32% M | 3.99 | −41.13 | 28.19 | 2.91 | 6.42 |
| WOF + EXT + 0.2% E + 32% M | 0.60 | −37.90 | 30.83 | 0.10 | 5.07 |

Figure 4:
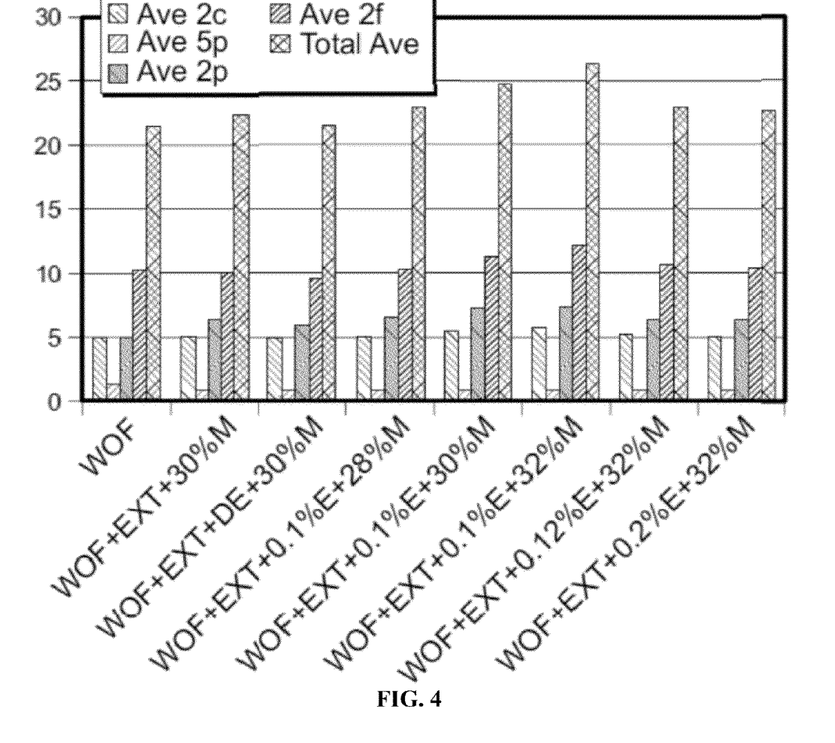
FIG. 4 compares the amount of avenanthramide identified in the oat flour as a result of the various processing conditions set forth in Table 2.

WOF: whole oat flour (unhydrolyzed);
EXT: extrusion;
E: enzyme;
DE: deactivated enzyme;
M: moisture;
Ave: avenanthramide In accordance with the results shown in the above table as well as FIG. 4, avenanthramide 2c has the highest antioxidant activity in vitro among the three major avenanthramides (2c, 2p, 2f). With respect to in vivo activity, avenanthramide 2p has the highest bioavailability. Extrusion alone increased the total avenanthramide content slightly (3.72%), but dramatically increased avenanthramide 2p content (27.79%). Enzymatic digestion increased total and individual avenanthramide content, including that of 2c, 2p, and 2f. At a fixed enzyme concentration (0.1%), moisture levels of 28%, 30% and 32% increased the total avenanthramide content by 6.47%, 15.26%, and 22.47% respectively compared with the whole oat flour. Moisture content or moisture levels were measured when the mixture entered the extruder. At a fixed moisture level of 32%, enzyme concentrations of 0.12% and 0.20% did not increase avenanthramide content when compared to an enzyme concentration of 0.1%.

Furthermore, the highly dispersible oat flour made in accordance with the instant methods also demonstrated an ability to suppress NF-κB. NF-κB is an immune response/inflammation trigger. In particular, reduced NF-κB is clinically linked to reduced chronic inflammation. Anti-inflammatory activity was measured by NF-κB inhibitory assay. Human 293T cells were cultured overnight in standard medium with fetal bovine serum and antibiotics followed by a 4-hour serum free to "starve" period. As one of ordinary skill in the art would recognize, "starved" cells are cells having a serum-free medium to eliminate the effects of fetal bovine serum and therefore the cells are more sensitive to TNF treatments. Afterward, cells were treated with TNF-α (100 ng/mL) and testing sample extracts for one hour at 37° C. with $CO_2$. Whole cell proteins were extracted and levels of NF-κB were measured using a TransAM NF-κB ELISA kit. The table below shows the results of the testing, comparing whole oat flour to SoluOat 90% and a blank. As used herein "SoluOat," "SoluOat flour," "SoluOat 90" or "regular SoluOat," whether singular or plural, shall mean 90% whole oat flour 5% sugar, 4.5% maltodextrin and 0.5% mixed tocopherol made in accordance with the methods set forth in the present disclosure.

| Description | Yield of NF-κB† | % Inhibition* |
|---|---|---|
| Whole Oat Flour, Flour | 170 | Not detected |
| SoluOat 90**, Flour | 125 | 26.59 |
| Blank | 171 | NA‡ |

Figure 5:
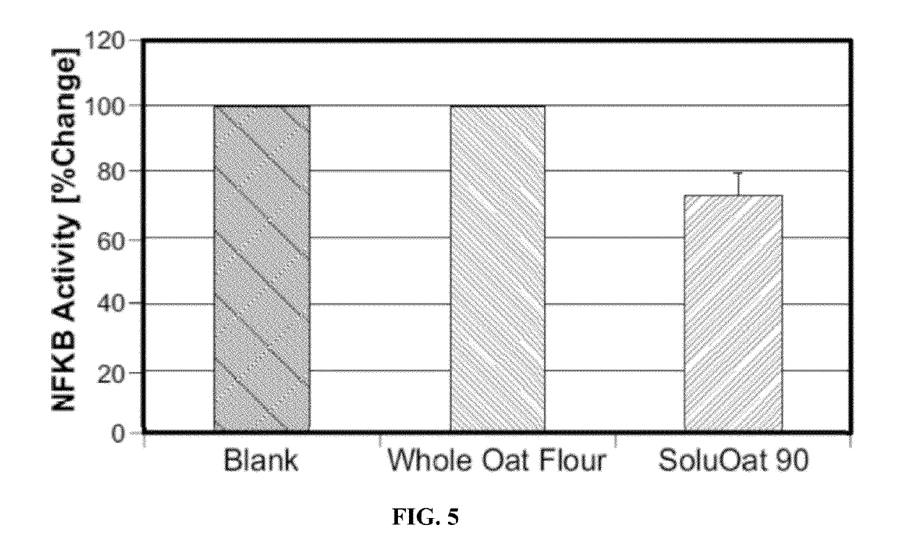
FIG. 5 depicts the percent change in NF-κB inhibition activity among whole oat flour, the methods described herein ("SoluOats"), and a blank.

*% inhibition was calculated against blank reading
**SoluOat 90 denotes that 90% of SoluOat was whole oat flour
†All samples were tested at concentration of 2 mg/mL
‡Not applicable FIG. 5 illustrates the percent of NF-κB inhibition in the samples.

This invention may be embodied in other specific forms without departing from the spirit or essential characteristics thereof. The foregoing embodiments, therefore, are to be considered in all respects illustrative rather than limiting the invention described herein. The scope of the invention is thus indicated by the appended claims, rather than by the foregoing description, and all changes that come within the meaning and range of equivalency of the claims are intended to be embraced therein.

We claim:

1. A highly dispersible whole grain oat flour containing about 20-35% more avenanthramides compared to native whole oat flour and wherein the whole grain oat flour is agglomerated following hydrolysis, pelletizing and milling.

2. The highly dispersible whole grain oat flour of claim 1 wherein the avenanthramide content of the flour is about 35% greater than native whole grain out flour.

3. The highly dispersible whole grain oat flour of claim 1 wherein the oat flour exhibits nuclear-factor kappa B inhibition activity wherein the nuclear-factor kappa B inhibition activity is at least about 25% greater than native whole grain oat flour.

4. A highly dispersible whole grain oat flour produced using the following process:
   a. combining a native whole grain oat flour starting mixture with an aqueous enzyme solution to form an enzyme starting mixture having a moisture content of 25 to 40 wt %;
   b. heating the enzyme starting mixture;
   c. adding the heated starting mixture to an extruder and extruding the mixture until the temperature of the mixture increases to about 260° F. to 300° F. wherein the enzyme is deactivated;
   d. pelletizing the extruded flour;
   e. drying the pelletized extruded flour;
   f. milling the pelletized extruded flour to a particle size of about 50-420 microns;
   g. agglomerating the milled extruded flour to a particle size of about 150-1000 microns
   wherein the highly dispersible whole grain oat flour contains at least 20% higher level of avenanthramides compared to native whole oat flour.

5. The highly dispersible whole grain oat flour of claim 4 wherein the enzyme is α-amylase.

6. The highly dispersible whole grain oat flour of claim 5 wherein the enzyme starting mixture comprises 0.01-0.5 wt % α-amylase.

7. The highly dispersible whole grain oat flour of claim 4 wherein the enzyme starting mixture comprises about 0.15 wt % α-amylase 8. The highly dispersible whole grain oat flour of claim 4 wherein the starting mixture further comprises sugar and optionally maltodextrin.

9. The highly dispersible whole grain oat flour of claim 4 wherein the moisture content of the enzyme starting mixture in the extruder is about 28-32%.

10. The highly dispersible whole grain oat flour of claim 4 wherein the avenanthramide content of the flour is about 35% greater than native whole grain oat flour.

11. The highly dispersible whole grain oat flour of claim 4 wherein the oat flour exhibits nuclear-factor kappa B inhibition activity wherein the nuclear-factor kappa B inhibition activity is at least about 25% greater than native whole grain oat flour.

12. The highly dispersible whole grain oat flour of claim 4 wherein following deactivation of the enzyme, the oat flour leaves the extruder.

13. The highly dispersible whole grain oat flour of claim 4 wherein the starting mixture further comprises mixed tocopherols.

* * * * *